US006432456B1

(12) United States Patent
Mori

(10) Patent No.: US 6,432,456 B1
(45) Date of Patent: Aug. 13, 2002

(54) CANCER CELL GROWTH SUPPRESSOR AND CELL DIFFERENTIATION INDUCER AND METHOD FOR MANUFACTURING THE SAME

(75) Inventor: Takeshi Mori, Nagoya (JP)

(73) Assignee: Laboratories for Intelligent Medical Remote Services, Aichi (JP)

( * ) Notice: Subject to any disclaimer, the term of this patent is extended or adjusted under 35 U.S.C. 154(b) by 0 days.

(21) Appl. No.: 09/969,646

(22) Filed: Oct. 4, 2001

(30) Foreign Application Priority Data

Oct. 4, 2000 (JP) ........................................ 2000-304987

(51) Int. Cl.⁷ ........................... A61K 35/78; A61K 9/00; A61K 47/00
(52) U.S. Cl. ........................ 424/760; 424/725; 424/400; 424/439
(58) Field of Search ................................ 424/760, 725, 424/400, 439

(56) References Cited

FOREIGN PATENT DOCUMENTS

JP   DW 1994-299652   *   8/1994
JP   10313849   *   12/1998

* cited by examiner

Primary Examiner—Christopher R. Tate
Assistant Examiner—Randall Winston
(74) Attorney, Agent, or Firm—Wenderoth, Lind & Ponack, L.L.P.

(57) ABSTRACT

A cancer cell growth suppressor or a cell differentiation inducer is provided which contains as an effective component a water-soluble component of *Capsicum Annuum L.Var.grossumn* which is a Solanacede plant. It is manufactured by mixing dried powder of fruits of *Capsicum Annuum L.Var.grossumn* and water for 40 hours or longer while maintaining them at normal temperature or higher, and obtaining an aqueous solution or a water-soluble component by separating the mixture into solid and liquid. A component having cancer cell growth suppressing properties or cell differentiation inducting properties, which could not be extracted sufficiently in a normal, short-time water-soluble component-extracting step, is reliably contained. It is used as a cancer cell growth suppressor or a cell differentiation inducer for treating cancer carriers or preventing recurrence.

20 Claims, 4 Drawing Sheets

FIG. 1

CD-DST method tumor tissue (operation specimen or biopsy material)
↓
treating for 30-minute to one-hour at 37 °C with cell dispersing enzyme EZ (digesting interstitial tissue and dispersing cell)
↓
preliminary cultivation in collagen gel coated flask (for 24 hours) (for removal of blood cells, necrosed cells and noncellular components)
↓
collagen gel droplet embedded cultivation (30 μl/drop)
↓
contacting with carcinostatic substance (under conditions close to blood AUC at the time of clinical dosage)
↓
non-serum cultivation (for seven days)(for suppression of growth of fibroblasts)
↓
dyeing and fixing of cells by neutral red dyeing
↓
analysis of cancer cells only on an image analyzing device and determination of sensitivity to carcinostatic substance

FIG. 2

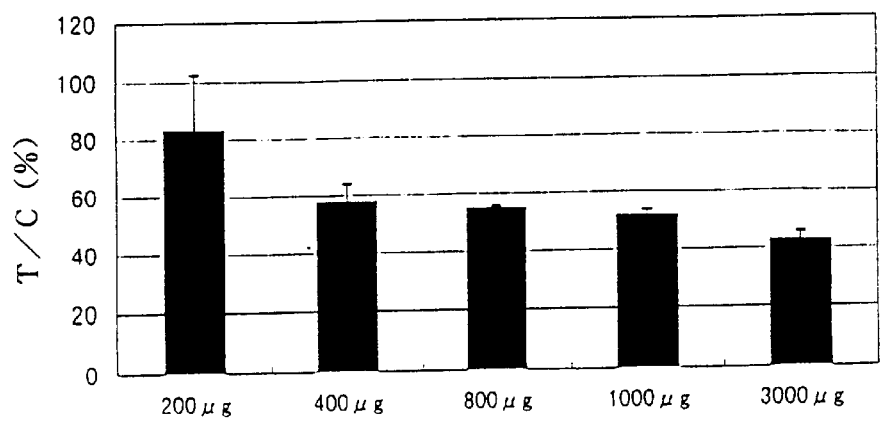

Differentiation inducing function of Toma-pi of different concentrations to promyelocytic leukemia cells (HL60)

Effect on promyelocytic leukemia cells (HL60) when used together with active vitamin D3

Effect on promyelocytic leukemia cells (HL60) when used together with active vitamin D3

CANCER CELL GROWTH SUPPRESSOR AND CELL DIFFERENTIATION INDUCER AND METHOD FOR MANUFACTURING THE SAME

BACKGROUND OF THE INVENTION

This invention relates to a cancer cell growth suppressor for suppressing the growth of cancer cells, and a cell differentiation inducer for promoting normal differentiation of human body cells, and a method of manufacturing the same.

Generally, substances having the function of erasing active oxygen to maintain and promote human health are attracting attention. Also, it is admitted that substances having such a function, such as vitamins and carotenoids, have effects on prevention of cancer.

For example, as a kind of capsicum of the Solanacede, there is one referred to as paprika or pimento. Its seed and peel contain capsaicin, which is a hot taste component, β-carotene, capsanthin, lutein and cryptoxanthin as carotenoid-family pigments, etc.

Also, red powdery paprikas produced by removing seeds and stalks from ripe fruits of pimentoes (occidental red peppers) such as Hungarian pimentoes and drying the remaining are widely used as food materials for spices. As a kind of Hungarian paprikas, *Capsicum Annum L.Var.grossumn* is known. It is also called paradicsom paprika.

Among paradicsom paprikas, besides pure-family species, there are species in which one of the largebell type, pimento type and Hungarian paprika type and largeneapolytan type is hybridized (hereinafter F1 species). Paradicsom paprikas include species obtained by hybridization of F1 species (hereinbelow referred to as quaternary hybridization species) and backcross species of such hydridization species (subsequent hybridization species. Hereinafter referred to as F2 species).

Capsaicin and carotenoid-family pigments, which are components of *Capsicum Annum L.Var.grossumn*, have effect of suppressing carcinogenic viruses. Japanese patent publication 10-236968 discloses that extracts of paradicsom paprikas extracted by use of acetone, and ones obtained by extracting from the extract by use of hexane (main component: capsanthin) inhibit canceration of cells in a concentration-dependent manner by using a mixed cultivation method of Epstein-Barr virus (EBV).

But conventional paprika components called *Capsicum Annum L.Var.grossumn* or paradicsom paprikas comprise only extracts extracted in an organic solvent, and for their water-soluble components, no details are known. Thus such components have never been positively used as effective components of carcinostatics or nutritional food supplements.

The organic solvent extracts disclosed in the above publication have only activation inhibiting functions for Epstein-Barr virus (anti-carcinogenesis promoter function). It has not been known whether they have a function of suppressing growth of cells that have already cancerated.

An object of the present invention is to provide a cancer cell growth suppressor which uses effective components of paprikas called *Capsicum Annum L.Var.grossumn* (or paradicsom paprikas), and which not only has effects of preventing canceration but also acts on cells that have already cancerated and can suppress their growth.

SUMMARY OF THE INVENTION

According to this invention, there are provided a cancer cell growth suppressor and a cell differentiation inducer which contain as an effective component a water-soluble component of *Capsicum Annuum L.Var.grossumn* of a Solanacede plant.

The cancer cell growth suppressor according to the present invention has as its effective component a water-soluble component of *Capsicum Annuum L.Var.grossumn*, and as will be apparent from the results of the below-described Examples, its cancer cell growth suppressing function has been reliably recognized. Thus, it is extremely useful not only as a drug to be taken for cancer prevention but as a drug for cancer carrier or for prevention of recurrence.

Also, the cell differentiation inducer according to this invention, which is extremely high in the ability of promoting normal differentiation of human body cells, is used not only as a nutritional food supplement or a food additive but also as a medicine.

According to this invention, there is also provided a method of manufacturing a cancer cell growth suppressor or a cell differentiation inducer which comprises the steps of mixing dried powder of fruits of *Capsicum Annuum L.Var-.grossumn* of a Solanacede plant for 40 hours or longer while maintaining them at normal temperature or higher, and separating the mixture into solid and liquid to obtain an aqueous solution or a water-soluble component for use as an effective component.

With the method of manufacturing the cancer cell growth suppressor or a cell differentiation inducer according to this invention, a component having a cancer cell growth suppressing property or differential inducing property, which would not be sufficiently extracted in an ordinary short-time water-soluble extracting step, can be extracted reliably. Thus, it is possible to efficiently manufacture a cancer cell growth suppressor or a cell differentiation inducer which contains an extremely useful component as a drug for treatment of cancer carriers or prevention of recurrence.

Other features and objects of the present invention will become apparent from the following description made with reference to the accompanying drawings, in which:

BRIEF DESCRIPTION OF THE DRAWINGS

FIG. 1 is an explanatory view showing an outline as to how to judge the carcinostatic sensitivity by CD-DST method;

FIG. 2 is a graph showing the growth suppressing rate (T/C%) for carcinoma cells of uterine cervix at different concentrations of a water-soluble component of *Capsicum Annuum L.Var.grossumn;*

*Annuum L.Var.grossumn* and the NBT reducing ability for leukemia cell strains.

DETAILED DESCRIPTION OF THE PREFERRED EMBODIMENT

Figure 3:
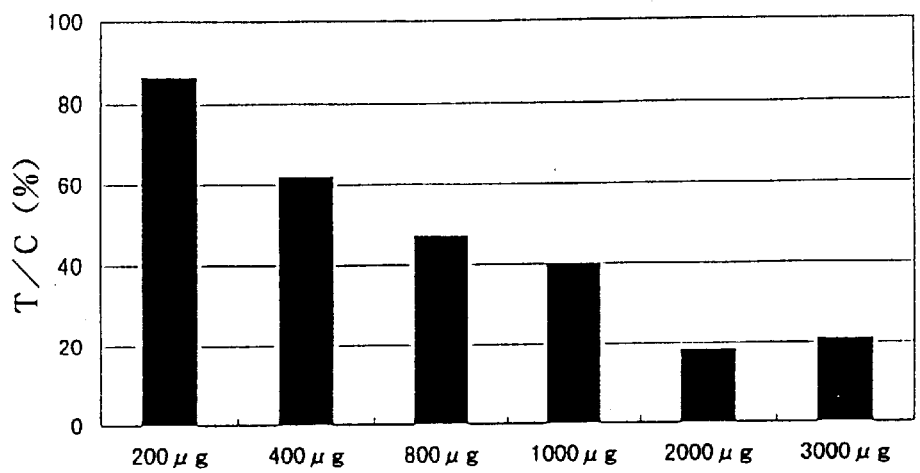
FIG. 3 is a graph showing the growth suppressing rate (T/C%) for carcinoma cells of the lung at different concentrations of a water-soluble component of *Capsicum Annuum L.Var.grossumn;*

*Capsicum Annuum L.Var.grossumn*, alias paradicsom paprika, referred to in this invention is a perennial plant of the Solanacede, and it produces fruits which are green, black, red or deep scarlet, and flat tomato-shaped. Their standard size is about 4 cm high, 9 cm diameter and 80–100 grams in weight. As fruits for raw material, ripe ones presenting green, red-black or deep scarlet color are suitable because completely ripe *Capsicum Annuum L.Var.grossumn* contains lycopene which is a kind of carotenoid, an antioxidant beneficial for human health, in more amounts than unripe ones. Paprikas called *Capsicum Annuum L.Var.grossumn* (or paradicsom paprika) in this invention includes, besides original species, pure-family species and F1 species, quaternary hybrid species, F2 species and subsequent hybrid species.

The components contained in such *Capsicum Annuum L.Var.grossumn* are safe as food. Since they have been safely used as food for a long time, they are vegetables or fruits comprising natural components safe for human bodies.

Fruits (edible portion) of the above plant are commercially available as fresh vegetables under the trade name Toma-pi. For example, with the manufacturing methods in the below-described Examples, it is possible to prepare dried powder suitable as extracted raw material.

In order to manufacture dried powder of *Capsicum Annuum L.Var.grossumn*, first, mud adhering to the fruit surface is washed away and unedible portions and rotten rotten portions are removed. The remaining portion is then subjected to sterilizing by heating them for 1 or 2 minutes at a temperature of 90–100° C. by an autoclave or boiling. In order to prevent degeneration of vitamins and carotenoids, not tap water containing a chlorine-family disinfectant but distilled water should be used for washing. Also, instead of using a sterilizer containing chlorine for sterilizing, heating sterilization is more preferable.

Next, *Capsicum Annuum L.Var.grossumn* is sliced to a thickness of about 3–8 mm and immediately subjected to hot air drying for 2 to 5 hours to dry it to the water content of about 5–7 wt %. Drying temperature should be set at 70–80° C., which is higher than normal drying temperature for vegetables such as tomatoes, to serve for sterilizing, too.

The dried article of *Capsicum Annuum L.Var.grossumn* obtained is put in a high-speed mill to coarsely screen, and the particles that have passed are further classified by sifting.

In order to obtain a water-soluble component of Capsicum Annuum L.Var.grossumn, a so-called water-extracting method is employed in which dried powder of *Capsicum Annuum L.Var.grossumn* are mixed with water, and after they are kept in contact with each other for a predetermined time at a predetermined temperature, followed by solid-liquid separation by filtering or centrifugal separation to obtain a liquid phase component.

Such a water-extracting method can be adjusted according to an extracted liquid preparation method employed for Shosaikoto, which is a kind of herb medicine. While such an extracted liquid preparation method (water extracting method) is described in detail in the below-described Examples, a well-known method may be employed which is described in [Digestive Organ] (volume 15(1), pages 79–84, issued in 1991).

The water-extracting method in the present invention is characterized in that while the extracting time in warm water in conventional water-extracting methods is about 30 minutes, a much longer extracting time, say 40 hours or over and preferably 48 hours at 37° C., is employed. By this extracting step, it is considered that a component having cancer cell growth suppressing property, which could not be extracted sufficiently in a conventional short-time water-soluble component-extracting step, is reliably extracted.

The concentration of the thus obtained water-soluble component added as a cancer cell growth suppressor may be adjusted to a suitable amount according to the kind of cells which are the target of treatment. Condensing as necessary is also preferable. It is difficult to set the most suitable concentration to a specific value beforehand. But in view of the below-described experiment results, as the effective concentration for suppressing growth of cancer cells, effects were positively recognized at 400 $\mu$g or over (400–3000 $\mu$g) for HeLa cells and at 800 $\mu$g or over (400–3000 $\mu$g) for other cells.

EXAMPLES

<Preparation of Dried Powder of *Capsicum Annuum L.Var.grossumn*>

Mud and the like adhering to fruits of *Capsicum Annuum L.Var.grossumn* was washed away, and unedible portions and rotten portions were removed. The remaining was subjected to sterilizing by heating them for 2 minutes at a temperature of 100° C. in an autoclave. Next, the sterilized fruits of *Capsicum Annuum L.Var.grossumn* were sliced to a thickness of about 5 mm and the water content was reduced to 6 wt % by immediately drying for two hours by hot air at 70–80° C. The dried fruit was put in a mill and sifted on a sieve of 40 mm. The passed particles were sifted by use of sieves of 40, 100, 200, 800 and 1500 meshes to obtain powder having a particle diameter of 10 $\mu$m or under (1500 mesh)(hereinafter referred to as Toma-pi powder).

<Extraction of a Water-soluble Component from the Dried powder of *Capsicum Annuum L.Var.grossumn*>

100 mg of the Toma-pi powder obtained in the above step was put in a 100 ml sterilized beaker, 10 ml of sterilized distilled water was added, and the mixture was shaked/stirred at 37° C. for 48 hours to incorporate. It was then divided by putting in 10 ml test tubes by 7–8 ml. It was centrifuged by a centrifugal machine for 20 minutes at 3000 revolutions per minute, and the supernatant liquid was filtered by use of a filter having an aperture of 8 $\mu$m. Further, it was put into a 10 ml test tube and centrifuged for 20 minutes at 3000 revolutions per minute. After carrying out this work three times, the sample was filtered by use of a filter having an aperture of 0.45 $\mu$m. Similarly, the filtrate was put in a 10 ml test tube and centifuged for 20 minutes at 3000 revolutions per minute. Thereafter, the supernatant liquid was filtered by use of a filter of 0.22 $\mu$m to obtain 100 mg/ml of condensed liquid (hereinafter referred to as Toma-pi water-extracted liquid).

<Test for confirming the Cancer Cell Growth Suppressing effect>

Employing a drug sensitivity test method (CD-DST method), Toma-pi water-soluble component condensed liquid of different concentrations was examined for growth suppressing effect at the contact time set at seven days.

The CD-DST method herein referred to is a well-known experiment method called a collagen gel drop method, and its steps are shown in FIG. 1. Its details are also described in "Establishment of Collagen Gel Droplet Embedded Culture Drug Sensitivity Test (CD-DST) and consideration about its clinical utility" in "Cancer and Chemical Treatment" (published in 1995, vol.22, 1933–1939 pages).

As a method of cultivating cancer cells, a human cancer cell first generation cultivation system kit (Plymaster made by Nitta Gelatine Co.), was used and cells were cultivated according to a normal method (reference document J. Jpn. Soc. Cancer Ther. 29(7) :946–956, 1994).

The growth suppressing effect was judged in terms of suppressing percentage (T/C%) which is the ratio of a treated group to an untreated group (control group). These results are shown in FIGS. 2–6. Units μg and mg shown in FIGS. 2–7 show the concentrations of Toma-pi water-soluble components in terms of the weight of Toma-pi powder (dried powder of *Capsicum Annuum L.Var.grossumn*) used as raw material for water extracting. It is hereinbelow referred to as "converted concentration of Toma-pi water-soluble components".

FIG. 2 shows the growth suppressing effect in experiments in which to cancer cells of the uterine cervix HeLa cells, Toma-pi water-extracted liquid was added in different concentrations and the cells were cultivated for 7 days. As will be apparent from the results shown in the graph, cancer cell growth suppressing effect was recognized, dependent upon the concentration of the Toma-pi water-soluble component. When the converted concentration of Toma-pi water-soluble component was 200 μg, it suppressed growth by 18%, and at 3000 μg, sufficient suppressing effect as high as 58% was observed.

FIG. 3 shows similar test results for carcinoma cells of the lung (A-549). When the converted concentration of Toma-pi water-soluble component was 200 μg, it suppressed growth by 15% and at 3000 μg, 80% growth suppression was observed.

Figure 4:
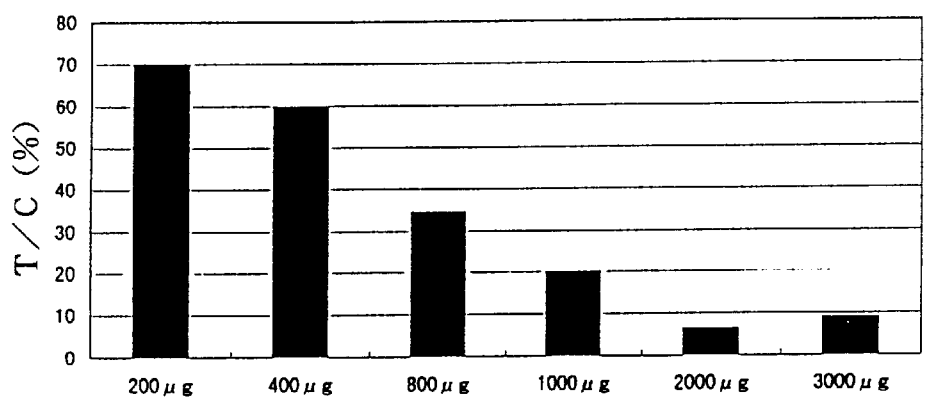
FIG. 4 is a graph showing the growth suppressing rate (T/C%) for carcinoma cells of pulmonary squamous cell carcinoma at different concentrations of a water-soluble component of *Capsicum Annuum L.Var.grossumn;*

FIG. 4 shows the results for pulmonary squamous cell carcinoma (PC-1 cells). Similarly, when the converted concentration of Toma-pi water-soluble component was 200 μg, it suppressed growth by 30% and at 3000 μg, 92% growth suppression was seen.

Figure 5:
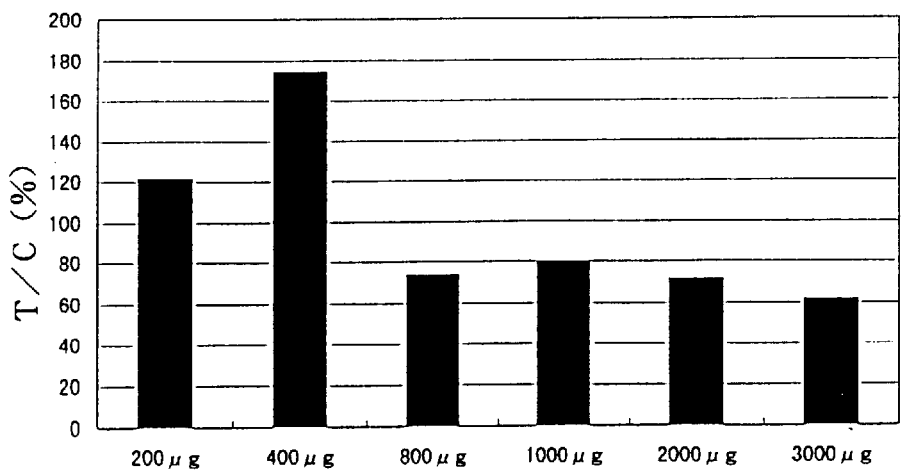
FIG. 5 is a graph showing the growth suppressing rate (T/C%) for carcinoma strain of the colon at different concentrations of a water-soluble component of *Capsicum Annuum L.Var.grossumn;*

FIG. 5 shows the results for carcinoma strain of the colon (Colo201 cells). When the converted concentrations of Toma-pi water-soluble component was 200 μg and 400 μg, neither growth suppression nor concentration dependency was observed. But at 800 μg, 35% growth suppression was observed, and at 3000 μg, 40% growth suppression was observed.

Figure 6:
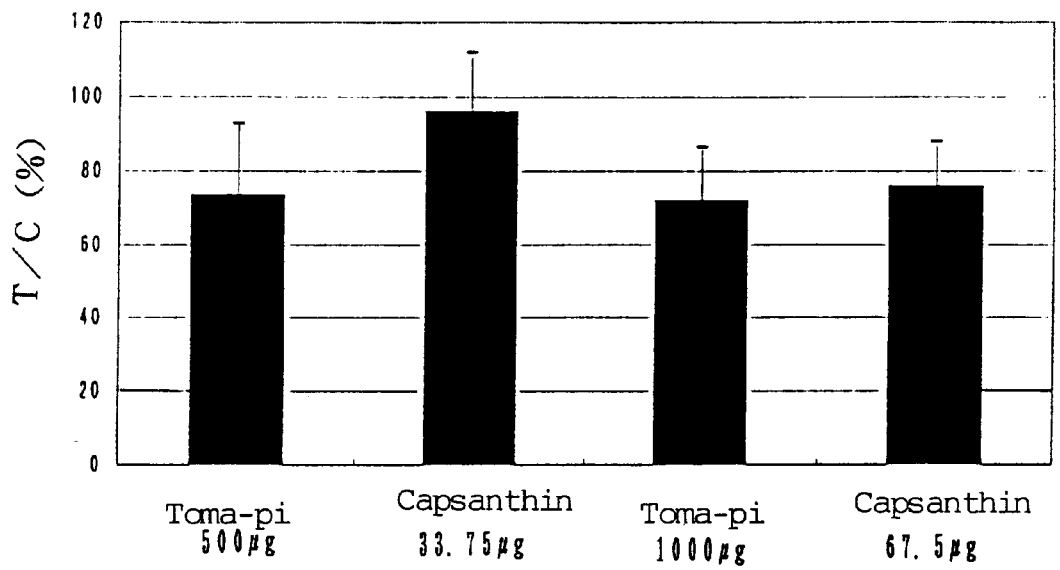
FIG. 6 is a graph showing the growth suppressing rate (T/C%) for carcinoma strain of the colon at different concentrations of a water-soluble component of *Capsicum Annuum L.Var.grossumn* or capsanthin.

FIG. 6 shows the results in which suppression by Toma-pi and capsanthin, which is one of major components of Toma-pi, was examined. When the converted concentrations of Toma-pi water-soluble component was 500 μg and 1000 μg, growth suppression of Colo201 cells was 24%, which was equivalent to 67.6 μg of capsanthin.

<Human leukemia Differentiation Inducing Test and Judgment of effect>

The differentiation inducing test using HL-60 cells, which are leukemia cells, was performed according to "New Cultured Cell Experiment Method" (written by Toshio Kuroki, on pages 286–289, published by Yodosha), "Jpn. J-Cancer" (Res. 81, 807–812, August 1990), and "Clinical Test Method" written by Izumi Kamei, page 358, published by Kinbara Shuppan) to examine the differentiation inducing ability with the NBT reducing ability as an index.

It is known that for HL60 cells, differentiation is induced by retinoic acid, DMSO or active type vitamin D3. Active type vitamin D3 (medicine for external use, treatment of psoriasis) and all-trans retinoic acid (ATRA) are used as oral medicine for treating leukemia. When leukemia cells differentiate, azurophile granules in the cells reduce. If they differentiate into granulocyte, cell nucleus segment. When they differentiate into monocyte/macrophage, the nucleus/cell ratio reduces, and they exhibit phagocytic capacity. As a convenient marker for differentiation induction of leukemia cells, one method is to measure nitro blune tetrazolium (NBT) reducing ability.

Figure 7:
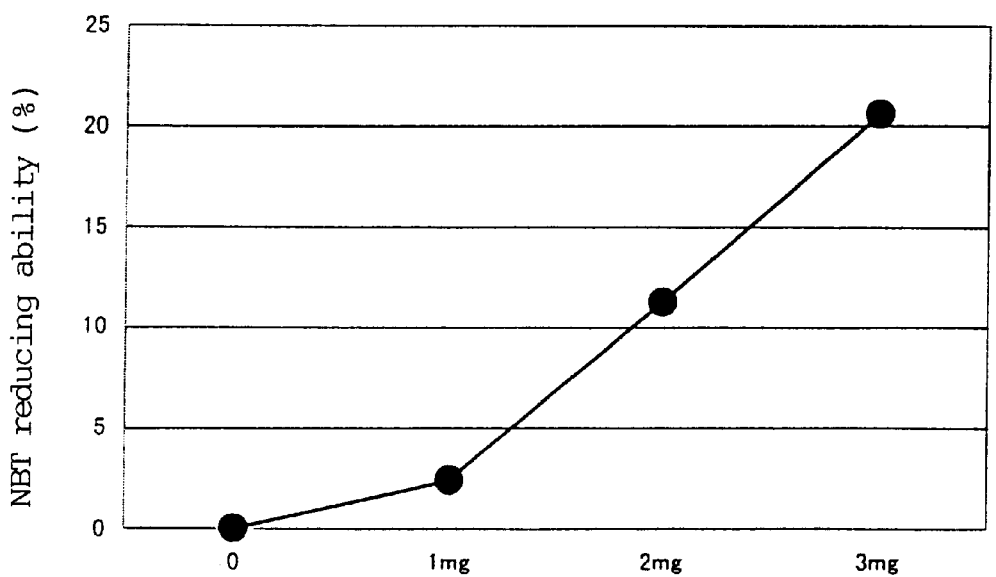
FIG. 7 is a graph showing the relation between the concentration of a water-soluble component of *Capsicum*

The NBT test uses the fact that when promyelocytic leukemia cells such as HL60 differentiate into monocyte/macrophage, production of active oxygen increases. That is to say, formation of insoluble formozan produced when NBT is reduced due to oxidation/reduction reaction by the active oxygen is used as a marker of differentiation. Active vitamin D3 has a differentiating ability at $10_{-9}$ to $10^{-6}$M, ATRA at $10^{-8}$ to $10^{-6}$M, and DMSO at 1.2 to 1.3%. At the respective maximum concentrations, they can differentiate by about 90% or over. Judging by the NBT reducing ability, the results were examined. FIG. 7 shows the results.

As will be apparent from the results shown in FIG. 7, when Toma-pi water extracted liquid of different concentrations was added, 3% NBT reducing ability was observed at the converted concentration of the Toma-pi water-soluble component of 1 mg, 13% at 2 mg and 21% at 3 mg in a concentration-dependent manner.

Figure 8:
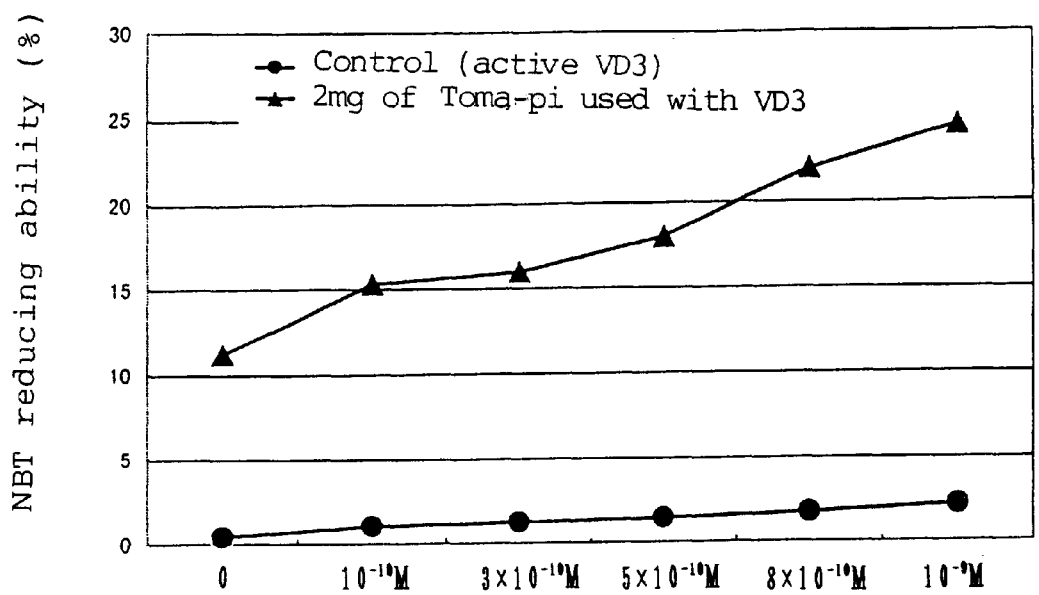
FIGS. 8 and 9 are graph showing the relation between the concentration of a water-soluble component of *Capsicum Annuum L.Var.grossumn* to which is added an active type vitamin D3 and the NBT reducing ability for leukemia cell strains.
Figure 9:
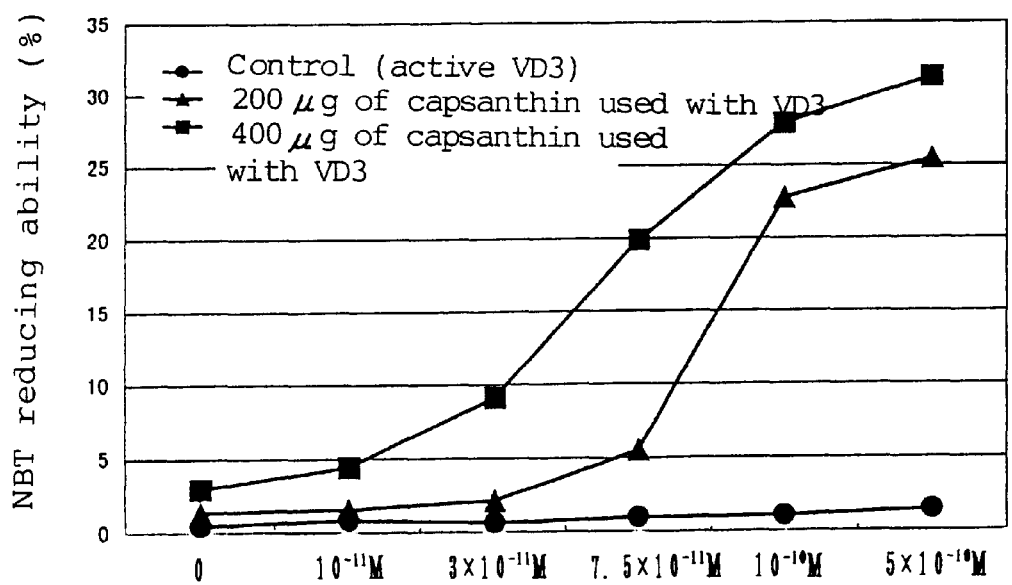

Also, in the human leukemia differentiation inducing test and the effect judging test, the differentiation induction effect for HL60 cells was examined when Toma-pi water extracted liquid of different concentration and active type vitamin D3 were both used. The results are shown in FIGS. 8 and 9.

As will be apparent from the results shown in these figures, for active type vitamin D3, the NBT reducing rate was about 5% at $10^9$M. Also, even alone, Toma-pi showed a positivity rate of 3–21%, and promoted differentiation at $10^{-10}$ M, at which active type vitamin D3 does not ordinarily show any differentiating ability, and, promoted differentiation at higher concentrations in a concentration-dependent manner (FIG. 8). Also, capsanthin promoted differentiation additionally at a low concentration of 400 μg and for active type vitamin D3 at a low concentration of $10^{-11}$M. 200 μg of capsanthin promoted differentiation from $7.5\times10^{-11}$M (FIG. 9).

Thus, by the study of not suppression of canceration promotor but the cell growth suppressing effect using the CD-DST method, the water extracted liquid of *Capsicum Annuum L.Var.grossumn* directly acted on cancer cells (for uterine cervix cancer, lung cancer, pulmonary squamous cell carcinoma), and suppressed their growth.

It has been found out that the growth suppressing effect depends on the concentration and the contact time. Also, it has been found out that it has a differentiation inducing function for human acute promyelocytic leukemia and if vitamin D3 is used together, its effect is strengthened. If it is taken as an antioxidant food processed as a food or beverage, or it is used together with a cancer prevention medicine and a carcinostatic, when it was taken with 4–12 g/day, its effect was seen after it was taken at least one week or longer. Also, if it is used for differentiation induction of e.g. human leukemia cells, when it was taken with 4–12 g/day, it was found out that its effect depended on the concentration of a carcinostatic or differentiation inducer.

As will be apparent from the above description, the cancer cell growth suppressor of the present invention contains as an effective component a water-soluble component of *Cap-*

*sicum Annuum L.Var.grossumn* of a Solanacede plant. Thus, it acts even on cells that have already cancerated to suppress its growth.

The cell differentiation inducer of the present invention contains as an effective component a water-soluble component of *Capsicum Annuum L.Var.grossumn* of a Solanacede plant. Thus, it induces cells to differentiate into normal cells, thereby preventing canceration of cells.

In the method of manufacturing a cancer cell growth suppressor or a cell differentiation inducer of the present invention, dried powder of fruits of Capsicum Annuum L.Var.grossumn and water are mixed for a predetermined long time at a predetermined temperature, and the obtained aqueous phase is added as an effective component. Thus, it is possible to efficiently manufacture a cancer cell growth suppressor or a cell differentiation inducer which reliably contains extremely useful components as a drug for treating cancer carriers or preventing recurrence.

What is claimed is:

1. A composition comprising an extract of *Capsicum Annuum L. Var. grossum* belonging to the Solanaceae family, which extract is obtained by immersing a dried powder of fruits of *Capsicum Annuum L. Var. grossum* in water for 40 hours or more to obtain a mixture, separating the mixture into a solid fraction and a liquid fraction, wherein the liquid fraction contains the extract of *Capsicum Annuum L. Var. grossum*, and optionally condensing the liquid fraction.

2. The composition according to claim 1, wherein the dried powder of fruits of *Capsicum Annuum L. Var. grossum* is prepared by washing the fruits, sterilizing the washed fruits, slicing the sterilized fruits, drying the sliced fruits, grinding the dried fruits, and passing the grinded fruits through a sieve, to obtain the dried powder.

3. The composition according to claim 1, wherein the water is distilled water.

4. The composition according to claim 1, wherein the dried powder is immersed in the water with agitation.

5. The composition according to claim 1, wherein the mixture is separated into the solid fraction and the liquid fraction using centrifugation or filtration or both.

6. The composition according to claim 1, wherein the liquid fraction has a cancer cell growth suppressor activity.

7. The composition according to claim 1, wherein the liquid fraction has a cell differentiation inducer activity.

8. The composition according to claim 1, which is a food or beverage.

9. The composition according to claim 1, which is a food supplement or food additive.

10. The composition according to claim 1, which is a medicine.

11. The composition according to claim 1, wherein the dried powder is immersed in the water at a temperature of 37° C. for 48 hours.

12. A method for making a composition comprising an extract of *Capsicum Annuum L. Var. grossum* belonging to the Solanaceae family, which comprising the steps of immersing a dried powder of fruits of *Capsicum Annuum L. Var. grossum* in water for 40 hours or more to obtain a mixture, separating the mixture into a solid fraction and a liquid fraction, wherein the liquid fraction contains the extract of *Capsicum Annuum L. Var. grossum*, and optionally condensing the liquid fraction.

13. The method according to claim 12, wherein the dried powder of fruits of *Capsicum Annuum L. Var. grossum* is prepared by washing the fruits, sterilizing the washed fruits, slicing the sterilized fruits, drying the sliced fruits, grinding the dried fruits, and passing the grinded fruits through a sieve, to obtain the dried powder.

14. The method according to claim 12, wherein the water is distilled water.

15. The method according to claim 12, wherein the dried powder is immersed in the water with agitation.

16. The method according to claim 12, wherein the mixture is separated into the solid fraction and the liquid fraction using centrifugation or filtration or both.

17. The method according to claim 12, wherein the liquid fraction has a cancer cell growth suppressor activity.

18. The method according to claim 12, wherein the liquid fraction has a cell differentiation inducer activity.

19. The method according to claim 12, wherein the composition is a food, beverage, food supplement, food additive or medicine.

20. The method according to claim 12, wherein the dried powder is immersed in the water at a temperature of 37° C. for 48 hours.

* * * * *